(12) United States Patent
Nishio et al.

(10) Patent No.: US 11,369,258 B2
(45) Date of Patent: Jun. 28, 2022

(54) LIGHT SOURCE SYSTEM, ENDOSCOPE SYSTEM, AND LIGHT SOURCE CONTROL METHOD

(71) Applicant: OLYMPUS CORPORATION, Tokyo (JP)

(72) Inventors: Masahiro Nishio, Hachioji (JP); Yoshihiko Watanabe, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 281 days.

(21) Appl. No.: 16/725,289

(22) Filed: Dec. 23, 2019

(65) Prior Publication Data
US 2020/0129055 A1   Apr. 30, 2020

Related U.S. Application Data

(63) Continuation of application No. PCT/US2017/023777, filed on Jun. 28, 2017.

(51) Int. Cl.
*A61B 1/06* (2006.01)
*H05B 47/10* (2020.01)

(52) U.S. Cl.
CPC ........... *A61B 1/0638* (2013.01); *H05B 47/10* (2020.01)

(58) Field of Classification Search
CPC ...... A61B 1/0638; H05B 47/10; H05B 47/17; H05B 47/165
See application file for complete search history.

(56) References Cited

U.S. PATENT DOCUMENTS

2013/0345517 A1* 12/2013 Morimoto ............ A61B 1/0661
600/178
2014/0293641 A1* 10/2014 Ito .......................... A61B 1/07
362/553
(Continued)

FOREIGN PATENT DOCUMENTS

CN         105377115 A      3/2016
JP         2009-277734 A   11/2009
(Continued)

OTHER PUBLICATIONS

Chinese Office Action dated Aug. 3, 2021 received in 201780092418.1.
(Continued)

*Primary Examiner* — Alexander H Taningco
*Assistant Examiner* — Pedro C Fernandez
(74) *Attorney, Agent, or Firm* — Scully, Scott, Murphy & Presser, P.C.

(57) ABSTRACT

A light source system includes an illumination device configured to generate illumination light, and a light source module having a function of supplying light to the illumination device and configured to be detachably attached to the illumination device. The illumination device includes a first light source and a first storage configured to store characteristic information of the first light source. The light source module includes a second light source and a second storage configured to store characteristic information of the second light source. The illumination device includes a control circuit configured to determine a driving condition of at least one of the first and second light sources, based on the characteristic information of the first and second light sources.

14 Claims, 7 Drawing Sheets

(56) References Cited

U.S. PATENT DOCUMENTS

| | | | | |
|---|---|---|---|---|
| 2016/0131892 A1* | 5/2016 | Tabata | ...................... | F21K 9/20 |
| | | | | 348/68 |
| 2016/0183771 A1* | 6/2016 | Viering | ................ | A61B 1/0684 |
| | | | | 600/110 |
| 2016/0324408 A1* | 11/2016 | Ohara | ................ | A61B 1/00006 |

FOREIGN PATENT DOCUMENTS

| | | | |
|---|---|---|---|
| JP | 2013-123477 | A | 6/2013 |
| JP | 2015-018640 | A | 1/2015 |
| JP | 2015-022834 | A | 2/2015 |
| JP | 2015-138712 | A | 7/2015 |

OTHER PUBLICATIONS

English translation of International Preliminary Report on Patentability dated Jan. 9, 2020, together with the Written Opinion received in related International Application No. PCT/JP2017/023777.

International Search Report dated Aug. 29, 2017 issued in PCT/JP2017/023777.

\* cited by examiner

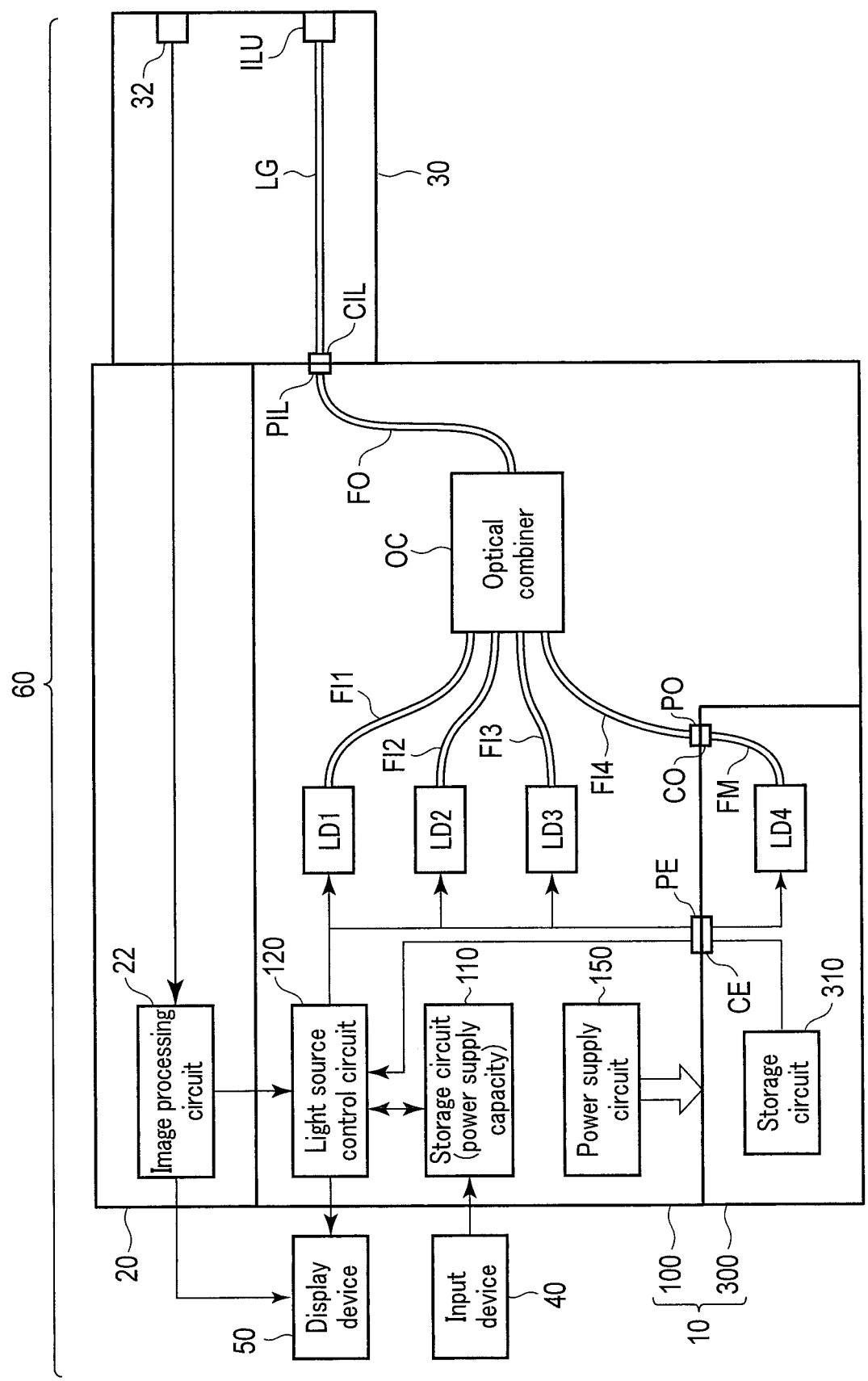
F I G. 1

LIGHT SOURCE SYSTEM, ENDOSCOPE SYSTEM, AND LIGHT SOURCE CONTROL METHOD

CROSS-REFERENCE TO RELATED APPLICATIONS

This application is a Continuation Application of PCT Application No. PCT/JP2017/023777, filed Jun. 28, 2017, the entire contents of which are incorporated herein by reference.

BACKGROUND OF THE INVENTION

1. Field of the Invention

The present invention relates to a light source system, an endoscope system, and a light source control method.

2. Description of the Related Art

In recent years, in observation devices such as an endoscope, an illumination device is used in which light emitted from a semiconductor light source is guided by a light guide member, and its color, its light intensity distribution, and the like are converted by a light converting member provided at the distal end of the light guide member, for example.

In such an illumination device, efforts are being made to improve the visibility of an observation object by appropriately selecting a peak wavelength, a spectrum shape, and the like.

In order to produce various types of illumination light according to the purpose, semiconductor light sources having different wavelength characteristics need to be combined to combine the light of the light sources and emit the combined light, and to further wavelength-convert the light by a wavelength converting member such as a fluorescent substance provided at the distal end and emit the wavelength-converted light.

For example, Jpn. Pat. Appln. KOKAI Publication No. 2009-277734 discloses an example of an illumination device as described above.

BRIEF SUMMARY OF THE INVENTION

A light source system according to the present invention includes an illumination device configured to generate illumination light, and a light source module having a function of supplying light to the illumination device and configured to be detachably attached to the illumination device. The illumination device includes at least one first light source and a first storage configured to store characteristic information of the first light source. The light source module includes at least one second light source and a second storage configured to store characteristic information of the second light source. The illumination device further includes a light source control circuit configured to determine a driving condition of at least one of the first light source and the second light source, based on the characteristic information of the first light source and the characteristic information of the second light source.

An endoscope system according to the present invention includes an illumination device configured to generate illumination light, a light source module having a function of supplying light to the illumination device and configured to be detachably attached to the illumination device, and an endoscope configured to emit the illumination light. The illumination device includes at least one first light source and a first storage configured to store characteristic information of the first light source. The light source module includes at least one second light source and a second storage configured to store characteristic information of the second light source. The illumination device further includes a light source control circuit configured to determine a driving condition of at least one of the first light source and the second light source, based on the characteristic information of the first light source and the characteristic information of the second light source.

A light source control method according to the present invention is of controlling a light source system including an illumination device including a first light source and configured to generate illumination light, and a light source module having a function of supplying light to the illumination device, configured to be detachably attached to the illumination device, and including a second light source. The method includes determining a driving condition of at least one of the first light source and the second light source, based on characteristic information of the first light source and characteristic information of the second light source, and driving at least one of the first light source and the second light source in accordance with the driving condition.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram schematically illustrating an endoscope system including a light source system according to a first embodiment of the present invention.

DETAILED DESCRIPTION OF THE INVENTION

First Embodiment

Figure 2:
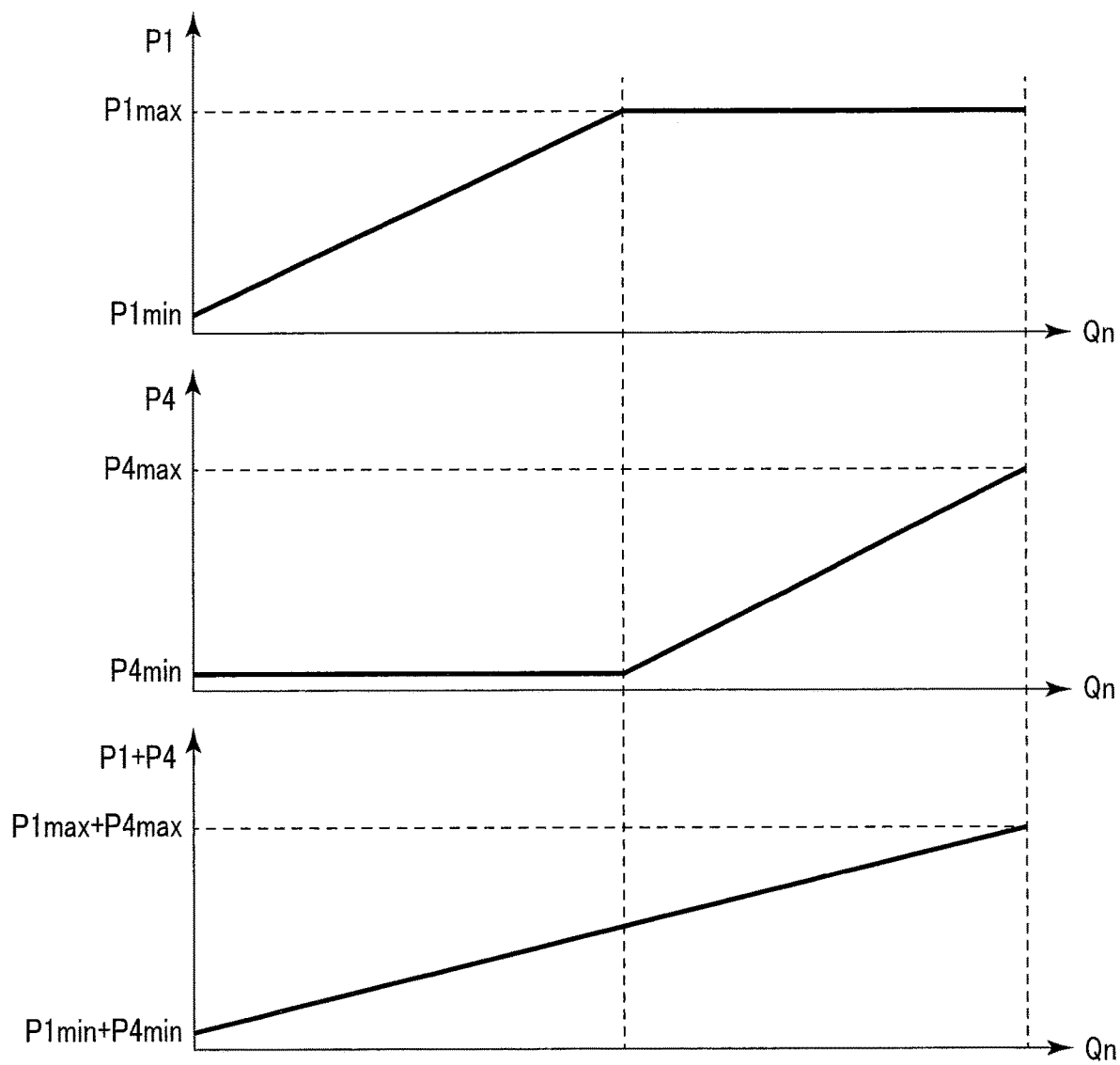
FIG. 2 illustrates the output light quantity of a light source in an illumination device, the output light quantity of a light source in a light source module, and the light quantity of combined light of both the light sources, according to an example of light quantity control.

FIG. 1 is a block diagram schematically illustrating an endoscope system including a light source system according to a first embodiment of the present invention.

<Endoscope System>

A light source system 10 configures a part of an endoscope system 60 in cooperation with an endoscope 30 configured to observe the interior of a tube of an observation object. The light source system 10 supplies the endoscope 30 with illumination light for illuminating the interior of the tube of the observation object.

The endoscope system 60 includes an image processing system 20 configured to process image information acquired by the endoscope 30, an input device 40 configured to allow information to be supplied to the light source system 10 from the outside, and a display device 50 configured to display information from the light source system 10 and the image processing system 20 in order to provide the information to the outside.

The light source system 10 includes an illumination device 100 configured to generate illumination light. The illumination device 100 includes an illumination light port PIL configured to output illumination light. The endoscope 30 includes an illumination light connector CIL configured to be connected to the illumination light port PIL of the illumination device 100.

The endoscope 30 further includes a light guide LG optically connected to the illumination light connector CIL and a light emitting unit ILU optically connected to the light guide LG. The light emitting unit is disposed at the distal end of the endoscope 30.

The illumination light connector CIL, light guide LG, and light emitting unit ILU constitute an illumination device configured to emit illumination light, in cooperation with the illumination device 100.

An optical element such as a diffusion plate for adjusting the distribution of the illumination light may be provided at the illumination light port PIL. This optical element may be provided at the light emitting unit ILU in place of the illumination light port PIL.

The illumination light output from the illumination light port PIL of the illumination device 100 enters the light guide LG through the illumination light connector, is guided by the light guide LG, reaches the light emitting unit ILU, and is emitted from the light emitting unit ILU to the exterior of the endoscope 30.

The endoscope 30 further includes an imaging element 32 configured to acquire image information of an observation object illuminated with illumination light emitted from the light emitting unit ILU. The imaging element 32 outputs the acquired image information to the image processing system 20.

The image processing system 20 includes an image processing circuit 22 configured to process image information supplied from the imaging element 32. The image processing circuit 22 outputs the processed image information to the display device 50. The image processing circuit 22 also outputs the processed image information to the light source system 10.

The display device 50 is configured to display image information supplied from the image processing circuit 22. The display device 50 is also configured to display information supplied from the light source system 10. As will be described later, the information supplied from the light source system 10 includes characteristic information of light sources LD1 to LD3 built in the illumination device 100, characteristic information of a light source LD4 mounted on a light source module 300, information of proper illumination light determined by a light source control circuit 120, a message to call attention when an incompatible light source module is attached to the illumination device 100, and the like.

The input device 40 is configured to allow a user to input various items of information including, for example, information of illumination light to be generated, in other words, information of an observation method to be applied to the endoscope system 60. The information input from the input device 40 is supplied to the light source system 10, for example.

<Light Source System>

The light source system 10 comprises the illumination device 100 configured to generate illumination light and the light source module 300 having a function of supplying light to the illumination device 100. The light source module 300 is configured to be detachably attached to the illumination device 100.

In the present embodiment, the light source system 10 comprises the illumination device 100 and one light source module 300, but the number of light source modules 300 attached to and detached from the illumination device 100 is not limited to one. For example, one of the light source modules prepared in advance may be attached to and detached from the illumination device 100. Alternatively, the illumination device 100 may be configured to allow light source modules to be detachably attached to the illumination device 100 at the same time. In other words, the light source system 10 may comprise the illumination device 100 and at least one light source module.

<Illumination Device>

The illumination device 100 includes three light sources LD1, LD2, and LD3, optical fibers FI1, FI2, and FI3 configured to guide light emitted from the light sources LD1, LD2, and LD3, an optical fiber FI4 configured to guide light supplied from the light source module 300, an optical combiner OC having a light combining function of combining the light guided by the optical fibers FI1 to FI4, and an optical fiber FO configured to guide the light output from the optical combiner OC to the illumination light port PIL.

In the present embodiment, the illumination device 100 includes three light sources LD1 to LD3, but the number of light sources is exemplary and may be less or more. That is, the illumination device 100 has only to include at least one light source.

The light sources LD1 to LD3 may each comprise a semiconductor light source, for example. The semiconductor light source may comprise a laser diode that is a narrowband light source, for example.

The light sources LD1 to LD3 have different peak wavelengths. The peak wavelengths of the light sources LD1 to LD3 belong to different color ranges, for example.

Here, that a light source has a peak wavelength A means that the light source emits light whose spectrum has a peak wavelength A. In addition, the light source itself does not have a peak wavelength, but for the sake of convenience, it is assumed that the peak wavelength of light emitted from the light source is abbreviated as the peak wavelength of the light source.

The illumination device 100 also includes a storage 110 having a function of storing various items of information, a light source control circuit 120 having a function of controlling the light sources LD1 to LD3, and a power supply circuit 150 having a power supply function.

The storage 110 stores characteristic information of the light sources LD1 to LD3. For example, the storage 110 stores wavelength characteristic information such as a peak wavelength, a line width, and a spectrum of light output from the light sources LD1 to LD3. The storage 110 stores information about the power supply capacity of the power supply circuit 150. The storage 110 can also store information input from the input device 40. The storage 110 can also store information about appropriate illumination light that can be emitted by a light source to be turned on, which is selected by the light source control circuit 120 as will be described later.

For example, the storage 110 may comprise an electronic circuit including at least one processor and at least one memory. For example, the memory may comprise a semiconductor memory (e.g. SRAM or DRAM), a register, a hard disk, or the like.

The storage 110 is configured to store various items of information input from the input device 40, such as information of illumination light to be generated, in other words, information of an observation method applied to the endoscope system 60.

<Light Source Module>

The light source module 300, which is detachably attached to the illumination device 100, includes a light source LD4, an optical fiber FM configured to guide light emitted from the light source LD4, and an optical link connector CO optically connected to the optical fiber FM.

In the present embodiment, the light source module 300 includes one light source LD4, but the number of light sources is exemplary and may be greater. That is, the light source module 300 has only to include at least one light source.

If the light source module 300 includes light sources, it includes optical fibers FM and optical connectors CO the number of which corresponds to the number of light sources, and the illumination device 100 includes optical connection ports PO and optical fibers FI4 the number of which corresponds to the number of light sources.

Like the light sources LD1 to LD3, the light source LD4 may comprise a semiconductor light source, for example. The semiconductor light source may comprise a laser diode that is a narrowband light source, for example.

For example, the peak wavelength of the light source LD4 in the light source module 300 may be the same as one of the peak wavelengths of the light sources LD1 to LD3. In this case, the light source LD4 contributes toward compensating for lack of light quantity of a light source (i.e. one of the light sources LD1 to LD3) having the same peak wavelength as that of the light source LD4.

Alternatively, the peak wavelength of the light source LD4 may differ from each of the peak wavelengths of the light sources LD1 to LD3. In addition, the peak wavelength of the light source LD4 may belong to the same color range as one of the color ranges to which the peak wavelengths of the light sources LD1 to LD3 belong, for example. In this case, the light source LD4 contributes to adjustment of the dominant wavelength. Alternatively, the peak wavelength of the light source LD4 may belong to a color range that differs from each of the color ranges to which the peak wavelengths of the light sources LD1 to LD3 belong. In this case, the light source LD4 contributes to generation of illumination light that cannot be generated by the combination of the light sources LD1 to LD3.

The light source module 300 also includes a storage 310 having a function of storing characteristic information of the light source LD4. The storage 310 stores wavelength characteristic information such as a peak wavelength, a line width, and a spectrum of the output light of the light source LD4.

With the light source module 300 attached to the illumination device 100, the light source system 10 further includes the light source LD4 in addition to the light sources LD1-LD3. In other words, the light sources LD1 to LD3 are light sources that are installed as standard in the light source system 10, and the light source LD4 is an optional light source added to light source system 10. That is, the light source module 300 is attached to the illumination device 100 in order to add a light source to the light source system 10.

The illumination device 100 includes an optical connection port PO for optical connection with the light source module 300 and an electrical connection port PE for electrical connection with the light source module 300. The optical connection port PO is optically connected to the optical combiner OC through the optical fiber FI4.

On the other hand, the light source module 300 includes an optical link connector CO to be connected to the optical connection port PO of the illumination device 100 and an electrical connector CE to be connected to the electrical connection port PE of the illumination device 100. The optical link connector CO is optically connected to the light source LD4 through the optical fiber FM.

The light source control circuit 120 built in the illumination device 100 is to be electrically connected to the storage 310 and the light source LD4 through the electrical connection port PE and the electrical connector CE. The optical combiner OC built in the illumination device 100 is to be optically connected to the light source LD4 through the optical connection port PO and the optical link connector CO. Furthermore, the power supply circuit 150 built in the illumination device 100 is to be also electrically connected to the light source module 300 through the electrical connection port PE and the electrical connector CE.

The connection ports PO and PE may include different ports corresponding to the specifications such as the output light quantity, control voltage, and heat capacity of the light source module 300.

The connection ports PO and PE may have a structure that cannot be connected if the specifications of the light source module 300 do not conform to the connection ports.

As described above, the illumination device 100 may be configured to allow light source modules to be detachably attached thereto at the same time. In this case, the illumination device 100 includes optical connection ports PO and optical fibers FI4 the number of which corresponds to the number of light source modules to be attached or detached at the same time.

«Light Source Control Circuit»

The light source control circuit 120 has a function of controlling the light source LD4 mounted on the light source module 300 in addition to a function of controlling the light sources LD1 to LD3 built in the illumination device 100.

For example, the light source control circuit 120 has a function of performing the following operations. The light source control circuit 120 reads information of illumination light to be generated and characteristic information of the light sources LD1 to LD3 from the storage 110 in the illumination device 100, and also reads characteristic information of the light source LD4 from the storage 310 in the light source module 300. The information of illumination light to be generated may be stored in advance in the storage 110, or may be input from the input device 40 and stored in the storage 110 as appropriate. In addition, the storage 110 may be configured to store in advance information indicating a relationship between an observation mode or an illumination mode and the information of illumination light to be generated, and to derive the information of illumination light to be generated based upon information of the observation mode or the illumination mode input from the input device 40. The light source control circuit 120 selects a light source (i.e. one or more of the light sources LD1 to LD4) to be turned on, based upon the information of illumination light to be generated. The light source control circuit 120 determines appropriate illumination light that can be emitted by a light source to be turned on. The light source control circuit 120 causes the storage 110 in the illumination device 100 to store the determined appropriate information. The light source control circuit 120 determines the driving condition of the light source to be turned on, based upon the characteristic information of the light source to be turned on. The light source control circuit 120 drives the light source to be turned on according to the determined driving condition.

For example, the light source control circuit 120 may comprise a computing unit including at least one processor and at least one memory. In this case, for example, the memory stores a program for causing the processor to fulfill the function of controlling the light sources LD1 to LD4. When the processor executes the program, the processor fulfills a function as the light source control circuit 120.

Although FIG. 1 depicts the light source control circuit 120 as a single unit, the light source control circuit 120 is not limited to the single unit but may comprise two or more units. In this case, the units cooperate with each other to perform a process. Some of the units may be disposed outside the housing of the illumination device 100. Furthermore, the units may be configured to perform a process in association with each other by wire, namely, through ordinary electrical wiring or may be configured to perform a process in association with each other wirelessly, namely, through a network.

«Power Supply Circuit»

The power supply circuit 150 has a power supply capacity for supplying power necessary for the operations of the illumination device 100 and the light source module 300. That is, the power supply circuit 150 can supply power to various electrical devices of the illumination device 100 including the light sources LD1 to LD3, storage 110, and light source control circuit 120, and can supply power to the light source module 300. The power supplied to the light source module 300 includes a drive signal supplied from the light source control circuit 120 to the light source LD4, and power required for the light source control circuit 120 to read information from the storage 310.

<Providing Function>

The light source module 300 operates using various functions of the illumination device 100. In other words, the illumination device 100 provides the light source module 300 with the functions of the illumination device 100 in order to operate the light source module 300. Hereinafter, the functions will be referred to as providing functions. That is, the light source module 300 operates using the providing functions of the illumination device 100. The providing functions of the illumination device 100 are also provided for the illumination device 100 itself.

The power supply function of the power supply circuit 150 is one of the providing functions. That is, upon receiving electric power from the illumination device 100, the light source module 300 operates.

The characteristic information of the light sources LD1 to LD3 built in the illumination device 100, the characteristic information of the light source LD4 mounted on the light source module 300, the information of the proper illumination light obtained by the light source control circuit 120, and the like are displayed on the display device 50. The display device 50 also displays a message to call attention and the like when an incompatible light source module is attached to the illumination device 100, for example.

(Operation)

Light emitted from the light sources LD1 to LD4 enters the optical combiner OC through the optical fibers FI1 to FI4. When at least two of the light sources LD1 to LD4 are turned on, the light that enter the optical combiner OC are combined into illumination light by the optical combiner OC. When only one of the light sources LD1 to LD4 is turned on, the light that enters the optical combiner OC itself is illumination light and passes through the optical combiner OC as it does. The illumination light emitted from the optical combiner OC is emitted from the light source system 10 through the optical fiber FO and the illumination light port PIL.

The illumination light emitted from the light source system 10 enters the endoscope 30 through the illumination light connector CIL, is guided to the light emitting unit ILU by the light guide LG, and is emitted from the light emitting unit ILU to the exterior of the endoscope 30.

As described above, the illumination device 100 includes the power supply circuit 150 having a power supply function. The storage 110 stores information of the power supply capacity of the power supply circuit 150.

The light source module 300 operates using the power supply function of the power supply circuit 150 of the illumination device 100. That is, in the present embodiment, the providing functions of the illumination device 100 include the power supply function of the power supply circuit 150.

The light source control circuit 120 determines the maximum drivable power of a light source to be turned on, based upon the capacity information of the providing functions of the illumination device 100, and determines the maximum output of the light source to be turned on. In the present embodiment in particular, the light source control circuit 120 determines a range of the quantity of light that is allowed to be output from the light source to be turned on, based upon information of the power supply capacity of the power source circuit 150. In addition, the light source control circuit 120 controls the output light quantity of the light source to be turned on, within the range of the quantity of light that is allowed to be output from the light source to be turned on.

When the light source to be turned on includes the light source LD4 mounted on the light source module 300, the light source control circuit 120 determines a range of the quantity of light that is allowed to be output from the light source LD4, based upon information of the power supply capacity of the power supply circuit 150. Furthermore, the light source control circuit 120 controls the output light quantity of the light source LD4 within the range of the quantity of light that is allowed to be output from the light source LD4.

If the light source module 300 is attached to the illumination device 100 when the illumination device 100 is activated, the light source control circuit 120 is configured to perform an operation of determining the range of the quantity of light that is allowed to be output from the light source to be turned on, e.g. the light source LD4, when the illumination device 100 is activated. If the light source module 300 is not attached to the illumination device 100 when the illumination device 100 is activated, the light source control circuit 120 is configured to perform the operation of determining the range of the quantity of light that is allowed to be output from the light source to be turned on, e.g. the light source LD4, when the light source module 300 is attached to the illumination device 100. If the endoscope 30 is not connected to the illumination device 100 when the illumination device 100 is activated, the light source control circuit 120 is configured to perform the operation of determining the range of the quantity of light that is allowed to be output from the light source to be turned on, e.g. the light source LD4, when the endoscope 30 is connected to the illumination device 100. Naturally, the operation of determining the range of the quantity of light that is allowed to be output from the light source LD4 is performed only in the case where the light source module 300 is attached to the illumination device 100 and the light source LD4 is included in a light source to be turned on.

SOME CONFIGURATION EXAMPLES OF LIGHT SOURCE MODULE

Some configuration examples of the light source module 300 will be described below. As described above, the light source control circuit 120 selects a light source to be turned on (e.g. one or more of the light sources LD1 to LD4) based upon information of illumination light to be generated. In the following description of the configuration examples of the light source module, the light source to be turned on includes at least the light sources LD1 and LD4, and the light source control circuit 120 controls the light sources LD1 and LD4.

Configuration Example 1 of Light Source Module

In this configuration example, the peak wavelength of the light source LD4 differs from the peak wavelengths of each of the light sources LD1 to LD3. Furthermore, the peak wavelength of the light source LD4 belongs to the same color range as the color range to which the peak wavelength of the light source LD1 belongs.

The light source control circuit 120 controls the output light quantity of the light source LD1 and the output light quantity of the light source LD4 so that the dominant wavelength of light obtained by combining the light emitted from the light source LD1 and the light emitted from the light source LD4 coincides with a target wavelength. The peak wavelength of the light source LD1 is stored in the storage 110 in the illumination device 100, and the peak wavelength of the light source LD4 is stored in the storage 310 in the light source module 300.

Information of the target wavelength may be prestored in the storage 110, or may be input from the input device 40 and stored in the storage 110 as appropriate. In addition, the storage 110 may be configured to store in advance information indicating a relationship between an observation mode or an illumination mode and the information of the target wavelength, and to derive the information of the target wavelength based upon information of the observation mode or the illumination mode input from the input device 40. Furthermore, based upon image information acquired by the imaging element 32 included in the endoscope 30, information of the target wavelength may be derived based on the color signal of an image such that the color of the image has a value suitable to observe the interior of a tube.

Assume that the peak wavelength of the light source LD1 is $\lambda$, the peak wavelength of the light source LD4 is $\lambda 4$, the output light quantity of the light source LD1 is P1, and the output light quantity of the light source LD4 is P4. The dominant wavelength $\lambda$ of the combined light is obtained by the relation $\lambda=(\lambda 1 P1+\lambda 4 P4)/(P1+P4)$.

The light source control circuit 120 determines the light quantity ratio that is the ratio of the output light quantity P1 of the light source LD1 to the output light quantity P4 of the light source LD4 such that the dominant wavelength $\lambda$ of the combined light coincides with the target wavelength.

Configuration Example 2 of Light Source Module

In this configuration example, the peak wavelength of the light source LD4 belongs to the same color range as the color range to which the peak wavelength of the light source LD1 belongs. For example, the peak wavelength of the light source LD4 coincides with that of the light source LD1.

The light source control circuit 120 controls the output light quantity of the light source LD1 and the output light quantity of the light source LD4 so that the light quantity of combined light obtained by combining the light emitted from the light source LD1 and the light emitted from the light source LD4 coincides with a target light quantity.

Information of the target light quantity may be prestored in the storage 110, or may be input from the input device 40 and stored in the storage 110 as appropriate. In addition, the storage 110 may be configured to store in advance information indicating a relationship between an observation mode or an illumination mode and the information of the target light quantity, and to derive the information of the target light quantity based upon information of the observation mode or the illumination mode input from the input device 40.

FIG. 2 illustrates the output light quantity of the light source LD1, the output light quantity of the light source LD4, and the light quantity of combined light of the light emitted from the light source LD1 and the light emitted from the light source LD4, according to the light quantity control by the present configuration example. Assume that the minimum output light quantity of the light source LD1 is P1min, the maximum output light quantity of the light source LD1 is P1max, the minimum output light quantity of the light source LD4 is P4min, and the maximum output light quantity of the light source LD4 is P4max.

When the target light quantity Qn is equal to or smaller than the rated output of the light source LD1, the light source control circuit 120 turns off the light source LD4 and turns on only the light source LD1 to increase or decrease the output light quantity P1 of the light source LD1 so as to obtain the target light quantity Qn. In other words, the light source control circuit 120 fixes the output light quantity of the light source LD4 to P4min and varies the output light quantity P1 of the light source LD1 between P1min and P1max.

When the target light quantity Qn is larger than the rated output of the light source LD1, the light source control circuit 120 turns on both the light sources LD1 and LD4 to drive the light source LD1 at the rated output and to increase or decrease the output light quantity of the light source LD4 so as to obtain the target light quantity Qn. In other words, the light source control circuit 120 fixes the output light quantity of the light source LD1 to P1max and varies the output light quantity P4 of the light source LD4 between P4min and P4max.

The order in which the light sources LD1 and LD4 are turned on may be reversed. That is, when the target light quantity Qn is equal to or smaller than the rated output of the light source LD4, the light source control circuit 120 turns off the light source LD1 to increase or decrease the output light quantity of the light source LD4. When the target light quantity Qn is larger than the rated output of the light source LD4, the light source control circuit 120 drives the light source LD4 at the rated output to increase or decrease the output light quantity of the light source LD1.

Configuration Example 3 of Light Source Module

In this configuration example, as in the foregoing configuration example 2, the peak wavelength of the light source LD4 belongs to the same color range as the color range to which the peak wavelength of the light source LD1 belongs. For example, the peak wavelength of the light source LD4 coincides with that of the light source LD1. The present configuration example differs from the foregoing configuration example 2 in the manner of the light quantity control.

The light quantity resolution of the light source LD4 is higher (has a larger increment step) than that of the light source LD1, and the maximum output of the light source LD4 is larger than that of the light source LD1. In addition, the light quantity resolution (increment step) of the light source LD4 is preferably equal to or less than the maximum light quantity of the light source LD1.

The light source control circuit 120 controls the output light quantity of the light source LD1 and the output light quantity of the light source LD4 so that the light quantity of combined light of the light emitted from the light source LD1 and the light emitted from the light source LD4 coincides with the target light quantity. The light source control circuit 120 thus controls the light sources LD1 and LD4 as will be described below.

Figure 3:
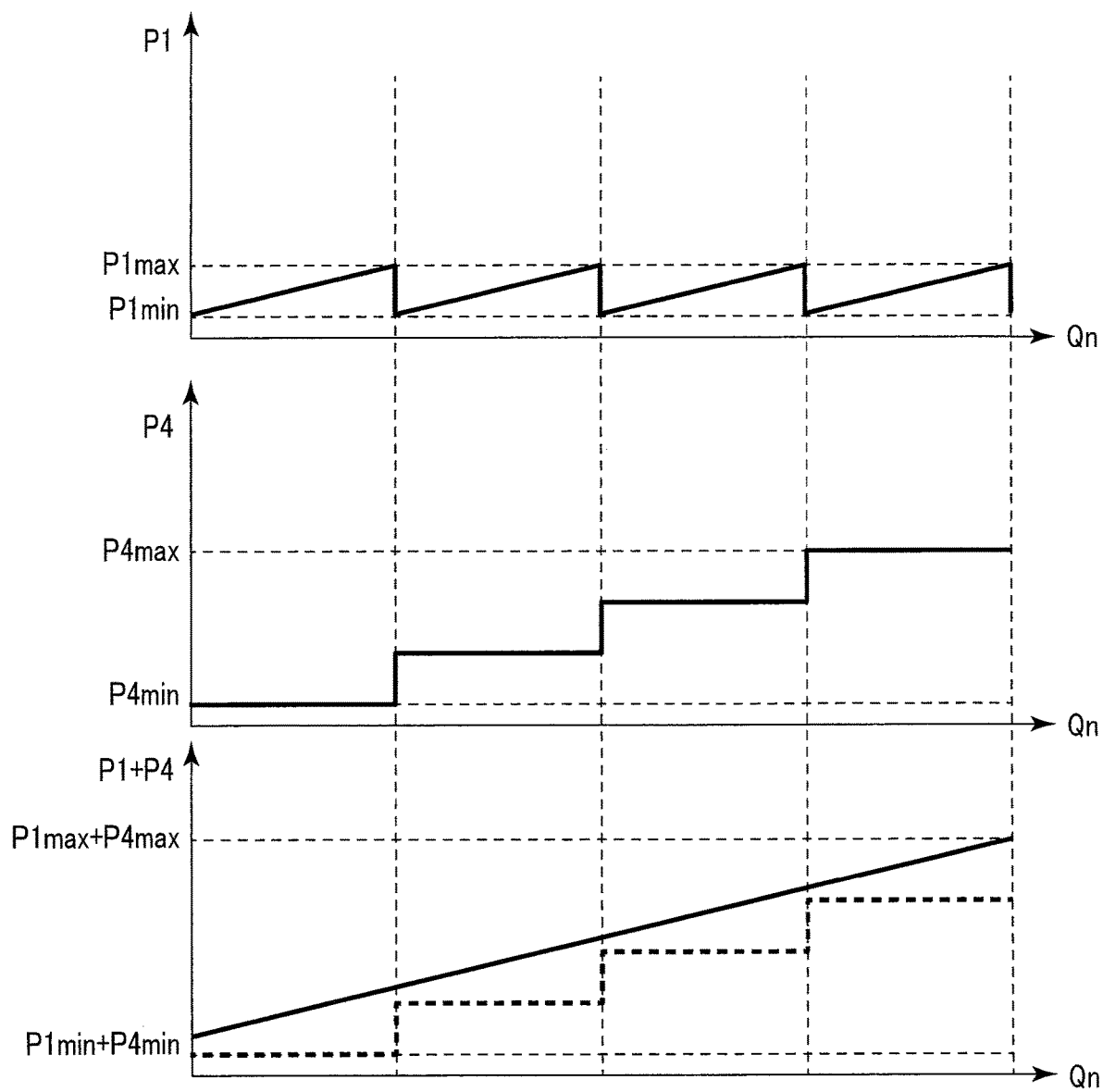
FIG. 3 illustrates the output light quantity of a light source in an illumination device, the output light quantity of a light source in a light source module, and the light quantity of combined light of both the light sources, according to another example of the light quantity control.

FIG. 3 illustrates the output light quantity of the light source LD1, the output light quantity of the light source LD4, and the light quantity of combined light of the light emitted from the light source LD1 and the light emitted from the light source LD4, according to the light quantity control by the present configuration example. Assume that the minimum output light quantity of the light source LD1 is P1min, the maximum output light quantity of the light source LD1 is P1max, the minimum output light quantity of the light source LD4 is P4min, and the maximum output light quantity of the light source LD4 is P4max. The light quantity resolution of the light source LD4 is equivalent to (P1max−P1min) and has a value of (P4max−P4min)/4.

The light source control circuit 120 first controls the output light quantity P4 of the light source LD4 in accordance with the target light quantity Qn. Specifically, the light source control circuit 120 increases the output light quantity P4 of the light source LD4 within a range not exceeding the target light quantity Qn. Then, the light source control circuit 120 varies the output light quantity P1 of the light source LD1 between P1min and P1max so as to obtain the target light quantity Qn.

For example, as the target light quantity Qn increases, the light source control circuit 120 increases the output light quantity P4 of the light source LD4 with a coarse resolution and increases the output light quantity P1 of the light source LD1 with a fine resolution within a certain range of the output light quantity P4 of the light source LD4. That is, the light source control circuit 120 controls the output light quantity of the light source LD4 with a low resolution and controls the output light quantity of the light source LD1 with a high resolution.

The light source LD4 having a low resolution and a large maximum light quantity and the light source LD1 having a high resolution and a small maximum light quantity are combined, so that the illumination device 100 can generate illumination light with compatibility between light quantity and resolution.

Configuration Example 4 of Light Source Module

Figure 4:
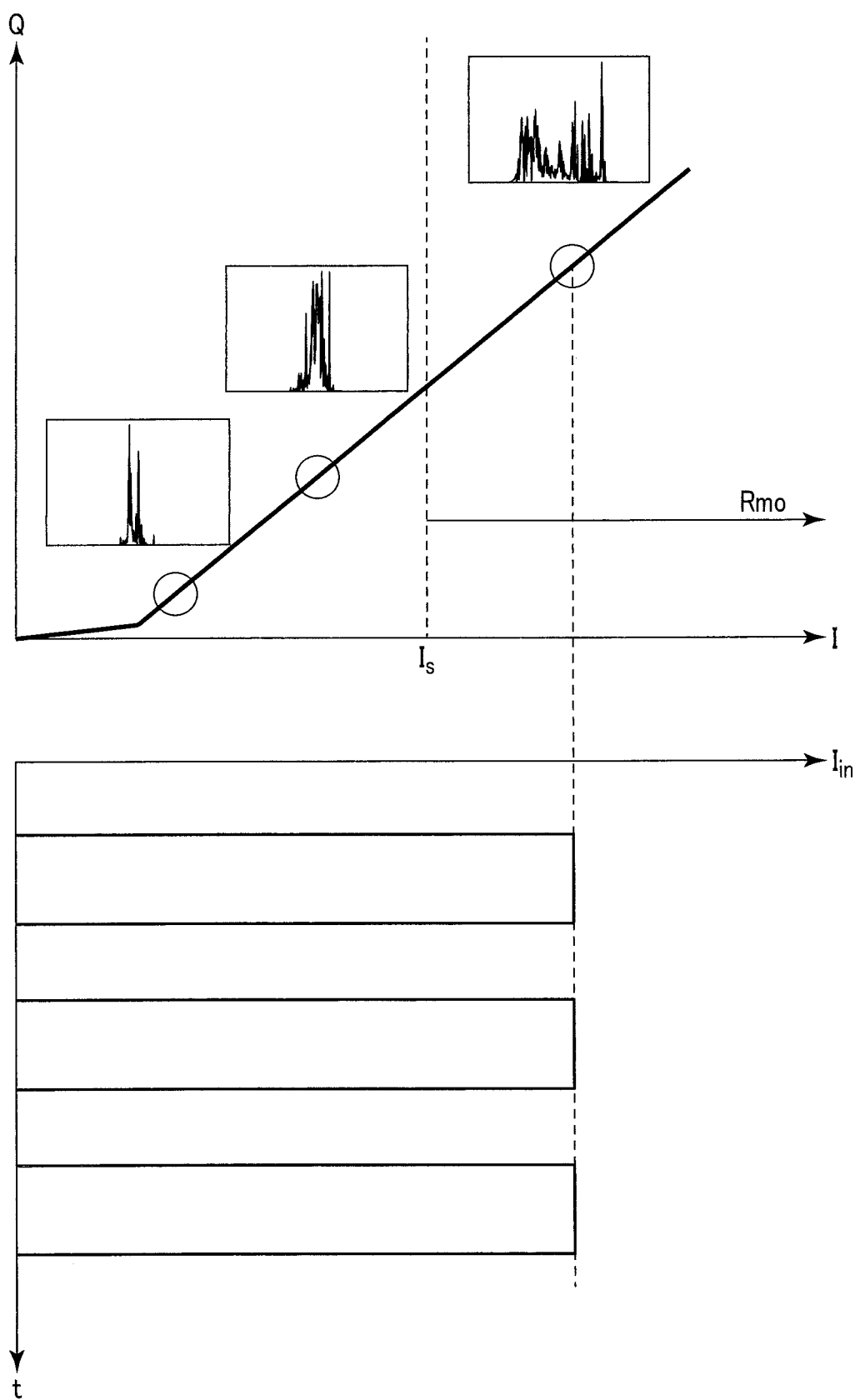
FIG. 4 illustrates the output light quantity and the oscillation mode with respect to the drive current of a laser diode and the pulse waveform of the drive input current with respect to time.

In the laser diode, the spread of wavelength spectrum of the output light varies with the increase and decrease in drive current. As the drive current increases, the wavelength spectrum is spread. FIG. 4 illustrates the output light quantity Q and the oscillation mode with respect to the drive current I of the laser diode and the pulse waveform of drive input current $I_{in}$ with respect to time t. For example, in the pulse modulation, light corresponding to the peak current of a pulse is emitted, as illustrated in FIG. 4.

Figure 5:
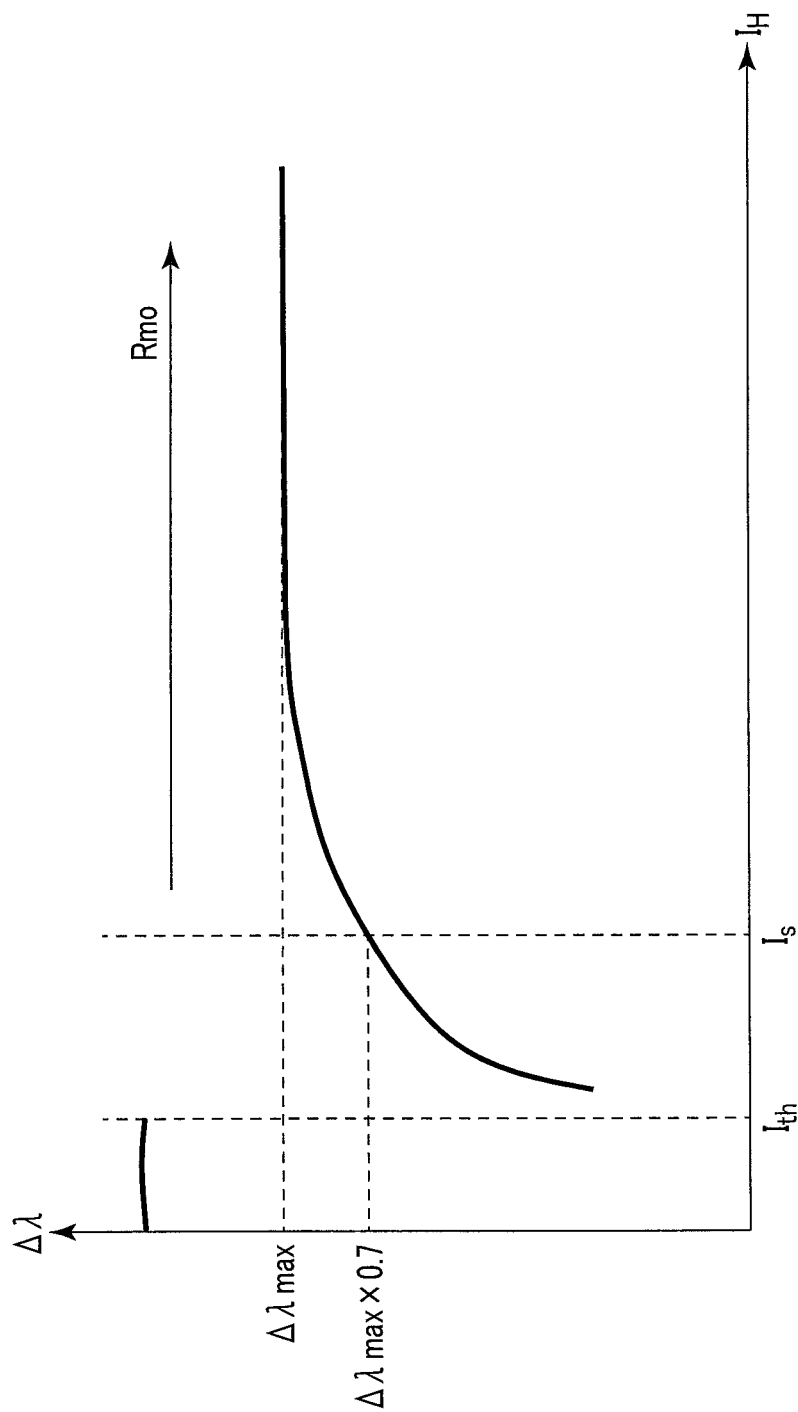
FIG. 5 illustrates a relationship between the width of a wavelength spectrum and the peak current of a pulse.

FIG. 5 illustrates a relationship between the width Δλ of a wavelength spectrum and the peak current $I_H$ of a pulse. As illustrated in FIG. 5, as the peak current $I_H$ of the pulse increases, the oscillation mode increases and the width Δλ of the wavelength spectrum increases. The width Δλ of the wavelength spectrum is defined by a wavelength interval at which the relative intensity of the wavelength spectrum with respect to the peak intensity is half, for example. A range in which the peak current $I_H$ of the pulse is smaller than the threshold current $I_{th}$ is recognized as a range in which the number of oscillation modes is one or small. A range in which the peak current $I_H$ of the pulse exceeds the multiple oscillation mode threshold current $I_s$ is recognized as a multiple oscillation mode range Rmo including a number of oscillation modes. The multiple oscillation mode threshold current $I_s$ is defined as 0.7 times the maximum wavelength spectrum width Δλmax in the multiple oscillation mode range Rmo, for example.

The oscillation mode increases because as the drive current to the laser diode increases, the carrier density and refractive index in a laser diode element are varied. The oscillation mode also increases because the carrier density and refractive index are also varied with an increase in the temperature of the interior of the laser diode element due to an increase in the quantity of emitted light.

The increase in the oscillation mode and the width Δλ of the wavelength spectrum indicates a decrease in temporal coherence, namely, a decrease in coherence. The speckles are thus reduced. As the drive current increases, the width Δλ of the wavelength spectrum increases and the coherence decreases. The speckles can thus be reduced. When the drive current decreases, the width Δλ of the wavelength spectrum decreases and the coherence increases. The speckles can thus be increased. Therefore, the width Δλ of the wavelength spectrum can be increased and decreased and the number of speckles can be controlled by the increase and decrease of Δλ current.

Using the above characteristics, for example, the light source control circuit 120 controls the output light quantity of the light source LD1 and the output light quantity of the light source LD4 so that the spread of the wavelength spectrum of light obtained by combining the light emitted from the light source LD1 and the light emitted from the light source LD4 coincides with a target spread.

Information of the target spread may be prestored in the storage 110 or may be input from the input device 40 and stored in the storage 110 as appropriate. Also, the storage 110 may be configured to store in advance information indicating a relationship between an observation mode or an illumination mode and information of the target spread, and to derive the information of the target spread based upon information of the observation mode or the illumination mode input from the input device 40.

In order to adjust the light quantity of the combined light and the width Δλ of the wavelength spectrum at the same time, the light source control circuit 120 may perform pulse modulation, set the pulse height of the drive current based on a target wavelength spectrum, and set the output light quantity of each of the light sources LD1 and LD4 based on a target light quantity.

Configuration Example of Illumination Device and Light Source Module

Operation Example 1 of Light Source System

As described above, the light sources LD1 to LD3 in the illumination device 100 have different peak wavelengths. The peak wavelengths of the light sources LD1 to LD3 belong to different color ranges, for example.

The light sources LD1 to LD3 have the following characteristics, for example. The light source LD1 has a peak wavelength in a blue range (wavelength range of 390 nm to 445 nm), the light source LD2 has a peak wavelength in a green range (wavelength range of 530 nm to 550 nm), and the light source LD3 has a peak wavelength in a red range (wavelength range of 600 nm to 750 nm). For example, the light source LD1 has a peak wavelength of 415 nm, the light source LD2 has a peak wavelength of 540 nm, and the light source LD3 has a peak wavelength of 638 nm.

For example, when the light source control circuit 120 turns on the light source LD1 having the peak wavelength in the blue range, the light source LD2 having the peak wavelength in the green range, and the light source LD3 having the peak wavelength in the red range at the same time, the light source system 10 can emit white illumination light suitable for white light observation.

In addition, when the light source control circuit 120 turns on the light source LD1 having the peak wavelength in the blue range and the light source LD2 having the peak wavelength in the green range at the same time, the light source system 10 can emit special illumination light suitable to detect hemoglobin in blood.

The light source LD4 of the light source module 300 has a peak wavelength of 780 nm, for example. Light having the peak wavelength of 780 nm is highly absorbed by indocyanine green (ICG), which is effective in identifying lung cancer by a fluorescence method, using the phenomenon of stasis in hepatocellular carcinoma tissue or in non-cancerous liver tissue excluded or displaced by tumors.

Therefore, when the light source control circuit 120 turns on only the light source LD4 having the peak wavelength of 780 nm, the light source system 10 can emit special illumination light suitable to detect a characteristic substance such as ICG.

Second Embodiment

Figure 6:
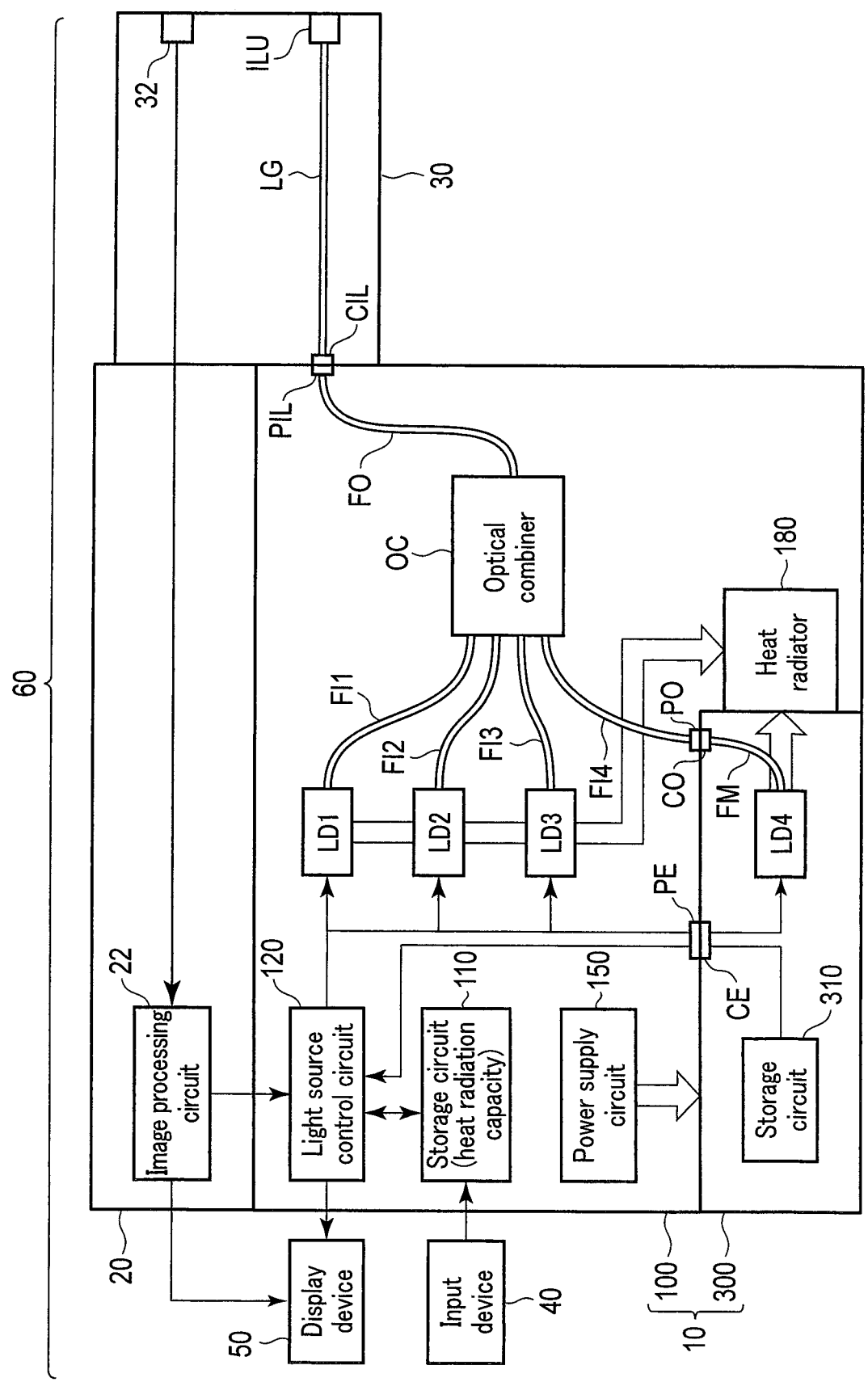
FIG. 6 is a block diagram schematically illustrating an endoscope system including a light source system according to a second embodiment of the present invention.

FIG. 6 is a block diagram schematically illustrating an endoscope system including a light source system according to a second embodiment of the present invention. In FIG. 6, the members like those in FIG. 1 are denoted by the same reference symbols, and their detailed descriptions will be omitted. The following descriptions focus on the differences from the first embodiment. That is, the portions not described in the following are like those in the first embodiment.

As illustrated in FIG. 6, the illumination device 100 according to the present embodiment includes a heat radiator 180. The heat radiator 180 has a heat radiating function of radiating heat from the light sources LD1 to LD3 in the illumination device 100 to the exterior of the light source system 10 to lower the temperature of the light sources LD1 to LD3. The heat radiator 180 also has a heat radiating function of radiating heat from the light source LD4 in the light source module 300 attached to the illumination device 100 to the exterior of the light source system 10 to lower the temperature of the light source LD4.

The storage 110 stores information of the heat radiation capacity of the heat radiator 180. For example, the information of the heat radiation capacity may be information of a quantity of heat that is equal to or smaller than the upper limit of the temperature of the device, a thermal resistance to the atmosphere of the heat radiator 180.

The light source module 300 operates using the heat radiating function of the heat radiator 180 of the illumination device 100. That is, in the present embodiment, the providing function of the illumination device 100 includes the heat radiating function of the heat radiator 180.

(Operation)

The light source control circuit 120 determines a quantity of heat that can be generated from a light source to be turned on, based on the information of the heat radiation capacity of the heat radiator 180, and determines a quantity of power that can be applied within a range of the quantity of heat. In other words, the light source control circuit 120 determines a range of the quantity of light that is allowed to be output from the light source to be turned on, based on the information of the heat radiation capacity of the heat radiator 180. Furthermore, the light source control circuit 120 controls the output light quantity of the light source to be turned on, within the range of the quantity of light that is allowed to be output from the light source to be turned on.

When the light source to be turned on includes the light source LD4 mounted on the light source module 300, the light source control circuit 120 determines the range of the quantity of light that is allowed to be output from the light source LD4, based on the information of the heat radiation capacity of the heat radiator 180. Furthermore, the light source control circuit 120 controls the output light quantity of the light source LD4 within the range of the quantity of light that is allowed to be output from the light source LD4.

(Modification 1)

When the light source to be turned on includes the light source LD4 and at least one of the light sources LD1 to LD3, the light source control circuit 120 may determine the range of the quantity of light that is allowed to be output from the light source LD4 in the following manner.

The information of the heat radiation capacity of the heat radiator 180 stored in the storage 110 is information of the overall heat radiation capacity of the heat radiator 180. The light source control circuit 120 determines the heat radiation capacity used by the light sources LD1 to LD3 to be turned on. The light source control circuit 120 subtracts the heat radiation capacity of the heat radiator 180 used by the light sources LD1 to LD3 to be turned on from the heat radiation capacity of the heat radiator 180 to set the subtraction result to the heat radiation capacity of the heat radiator 180 that the light source LD4 can use. The light source control circuit 120 determines the range of the quantity of light that is allowed to be output from the light source LD4, based on the information on the heat radiation capacity of the heat radiator 180 that the light source LD4 can use.

Third Embodiment

The configuration of a light source system 10 according to the present embodiment is substantially the same as that of the light source system 10 according to the first embodiment in terms of hardware. The light source system 10 according to the present embodiment differs from the light source system 10 according to the first embodiment in the providing function and its related operation.

Figure 7:
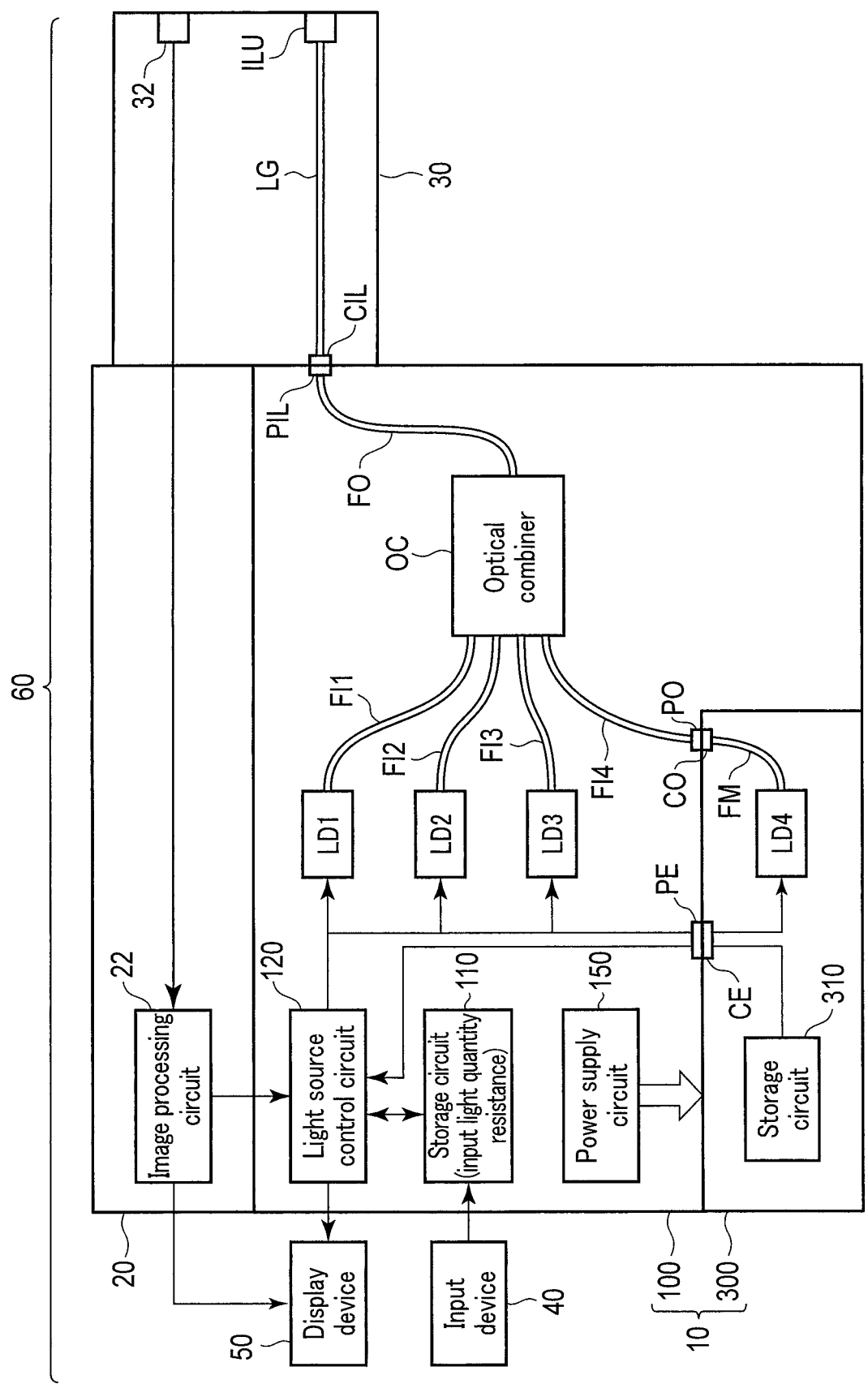
FIG. 7 is a block diagram schematically illustrating an endoscope system including a light source system according to a third embodiment of the present invention.

FIG. 7 is a block diagram schematically illustrating an endoscope system including a light source system according to a third embodiment of the present invention. In FIG. 7, the members like those in FIG. 1 are denoted by the same reference symbols, and their detailed descriptions will be omitted. The following descriptions focus on the differences from the first embodiment. That is, the portions not described in the following are like those in the first embodiment.

As described above, the illumination device 100 includes the optical combiner OC having the light combining function of combining the light emitted from the light sources LD1 to LD3 built in the illumination device 100 and the light emitted from the light source LD4 mounted on the light source module 300.

The storage 110 stores information of the light resistance of the optical combiner OC as information of the light combining capacity of the optical combiner OC. For example, the information of the light resistance may be information of the upper limit value of the quantity of light that can be input to the optical combiner OC. Alternatively, the information of the light resistance may be an upper limit value of the light quantity including the light resistance of the optical connector CO and the optical connection port PO connecting the illumination device 100 and the light source module 300.

The upper limit value of the quantity of light that can be input to the optical combiner OC has different value for each of the peak wavelengths of the light sources LD1 to LD4. Thus, the storage 110 may store an upper limit value of the quantity of light that can be input to the optical combiner OC corresponding to each of the peak wavelengths of the light sources LD1 to LD4, for example.

The light source module 300 operates using the light combining function of the optical combiner OC included in the illumination device 100. That is, in the present embodiment, the providing function of the illumination device 100 includes the light combining function of the optical combiner OC.

(Operation)

The light source control circuit 120 determines the maximum power that can drive the light source to be turned, based on the information of the light resistance of the optical combiner OC, and determines a range of the quantity of light that is allowed to be output from the light source to be turned on. Furthermore, the light source control circuit 120 controls the output light quantity of the light source to be turned on, within the range of the quantity of light that is allowed to be output from the light source to be turned on.

When the light source to be turned on includes the light source LD4 mounted on the light source module 300, the light source control circuit 120 determines the range of the quantity of light that is allowed to be output from the light source LD4, based on the information of the light resistance of the optical combiner OC. Furthermore, the light source control circuit 120 controls the output light quantity of the light source LD4 within the range of the quantity of light that is allowed to be output from the light source LD4.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source system comprising:
   an illumination device configured to generate illumination light; and
   a light source module having a function of supplying light to the illumination device and configured to be detachably attached to the illumination device,
   wherein:
   the illumination device comprises a first light source and a first storage configured to store characteristic information of the first light source;
   the light source module comprises a second light source and a second storage configured to store characteristic information of the second light source;
   the illumination device further comprises a light source control circuit configured to determine a driving condition of at least one of the first light source and the second light source, based on the characteristic information of the first light source and the characteristic information of the second light source;
   the illumination device further comprises a power supply circuit having a power supply function necessary for operations of the illumination device and the light source module;
   the light source module is configured to operate using a providing function of the illumination device;
   the providing function of the illumination device is the power supply function of the power supply circuit;
   the first storage is configured to store information of a power supply capacity of the power supply circuit; and
   the light source control circuit is configured to determine a range of quantity of light that is allowed to be output from the second light source, based on the information of the power supply capacity of the power supply circuit.

2. The light source system according to claim 1, wherein:
   the light source control circuit is configured to determine the range of quantity of light that is allowed to be output from the second light source, based on the capacity information of the providing function of the illumination device, to control an output light quantity of the second light source within the range of quantity of light that is allowed to be output from the second light source.

3. The light source system according to claim 1, wherein:
   the illumination device further includes a heat radiator having a heat radiating function of radiating heat from the first light source and the second light source;
   the light source module is configured to operate using another providing function of the illumination device;
   the another providing function of the illumination device is the heat radiating function of the heat radiator;
   the first storage is configured to store information of a heat radiation capacity of the heat radiator; and the light source control circuit is configured to determine the range of quantity of light that is allowed to be output from the second light source, based on the information of the heat radiating capacity of the heat radiator.

4. The light source system according to claim 1, wherein:
the illumination device comprises an optical combiner having a light combining function of combining light emitted from the first light source and light emitted from the second light source;
the light source module is configured to operate using another providing function of the illumination device;
the another providing function of the illumination device is the light combining function of the optical combiner;
the first storage is configured to store information of light resistance of the optical combiner; and
the light source control circuit is configured to determine the range of quantity of light that is allowed to be output from the second light source, based on the information of light resistance of the optical combiner.

5. The light source system according to claim 1, wherein:
the providing function of the illumination device is provided for the illumination device; and
the light source control circuit is configured to subtract capacity of a providing function used by the first light source from capacity of the providing function of the illumination device to make capacity of a providing function used by the second light source, and to determine the range of quantity of light that is allowed to be output from the second light source, based on the capacity of the providing function.

6. The light source system according to claim 3, wherein the light source control circuit is configured to control an output light quantity of the first light source and an output light quantity of the second light source so that a dominant wavelength of light obtained by combining light emitted from the first light source and light emitted from the second light source coincides with a target wavelength.

7. The light source system according to claim 3, wherein the light source control circuit is configured to control an output light quantity of the first light source and an output light quantity of the second light source so that a quantity of light obtained by combining light emitted from the first light source and light emitted from the second light source coincides with a target light quantity.

8. The light source system according to claim 3, wherein the light source control circuit is configured to control an output light quantity of the first light source and an output light quantity of the second light source so that a spread of a wavelength spectrum of light obtained by combining light emitted from the first light source and light emitted from the second light source coincides with a target spread.

9. The light source system according to claim 6, wherein the light source control circuit is configured to perform an operation of determining the range of quantity of light that is allowed to be output from the second light source when the light source module is attached to the illumination device.

10. The light source system according to claim 6, wherein the light source control circuit is configured to perform an operation of determining the range of quantity of light that is allowed to be output from the second light source when the illumination device is activated.

11. The light source system according to claim 6, wherein:
the illumination device comprises an illumination light port configured to output illumination light;
the illumination light port is configured to be connected an illumination light connector of an endoscope; and
the light source control circuit is configured to perform an operation of determining the range of quantity of light that is allowed to be output from the second light source when the endoscope is connected to the illumination device.

12. The light source system according to claim 7, wherein the light source control circuit is configured to control the output light quantity of one of the first light source and the second light source with a low resolution, and to control the output light quantity of the other of the first light source and the second light source with a high resolution.

13. An endoscope system comprising:
an illumination device configured to generate illumination light;
a light source module having a function of supplying light to the illumination device and configured to be detachably attached to the illumination device; and
an endoscope configured to emit the illumination light, wherein:
the illumination device comprises first light source and a first storage configured to store characteristic information of the first light source;
the light source module comprises second light source and a second storage configured to store characteristic information of the second light source;
the illumination device further comprises a light source control circuit configured to determine a driving condition of at least one of the first light source and the second light source, based on the characteristic information of the first light source and the characteristic information of the second light source;
the illumination device further comprises a power supply circuit having a power supply function necessary for operations of the illumination device and the light source module;
the light source module is configured to operate using a providing function of the illumination device;
the providing function of the illumination device is the power supply function of the power supply circuit;
the first storage is configured to store information of a power supply capacity of the power supply circuit; and
the light source control circuit is configured to determine a range of quantity of light that is allowed to be output from the second light source, based on the information of the power supply capacity of the power supply circuit.

14. A method of controlling a light source system comprising:
an illumination device configured to generate illumination light; and
a light source module having a function of supplying light to the illumination device and configured to be detachably attached to the illumination device,
wherein:
the illumination device comprises:
a first light source;
a power supply circuit having a power supply function necessary for operations of the illumination device and the light source module; and
a first storage configured to store characteristic information of the first light source and information of a power supply capacity of the power supply circuit; and the light source module comprises a second light source and a second storage configured to store characteristic information of the second light source, wherein the method comprises:

determining, by the illumination device, a driving condition of at least one of the first light source and the second light source, based on the characteristic information of the first light source and the characteristic information of the second light source;

operating the light source module using a providing function of the illumination device, the providing function of the illumination device being the power supply function of the power supply circuit; and determining, by the illumination device, a range of quantity of light that is allowed to be output from the second light source, based on the information of the power supply capacity of the power supply circuit.

* * * * *